(12) United States Patent
Levin

(10) Patent No.: US 6,551,313 B1
(45) Date of Patent: Apr. 22, 2003

(54) ELECTROSURGICAL INSTRUMENT WITH SEPARATE CUTTING AND COAGULATING MEMBERS

(76) Inventor: John M. Levin, 819 Chauncey Rd., Narberth, PA (US) 19072

( * ) Notice: Subject to any disclaimer, the term of this patent is extended or adjusted under 35 U.S.C. 154(b) by 0 days.

(21) Appl. No.: 09/847,119

(22) Filed: May 2, 2001

(51) Int. Cl.$^7$ ................................................ A61B 18/18
(52) U.S. Cl. ............................ 606/45; 606/47; 606/48; 606/49; 606/50
(58) Field of Search ............................... 606/32, 34, 40, 606/41, 42, 45, 46, 47, 48, 49, 50

(56) References Cited

U.S. PATENT DOCUMENTS

| | | |
|---|---|---|
| 4,051,855 A | 10/1977 | Schneiderman |
| 4,711,239 A | 12/1987 | Sorochenko et al. |
| 4,911,159 A | 3/1990 | Johnson et al. |
| 5,035,695 A | 7/1991 | Weber, Jr. et al. |
| 5,098,430 A | 3/1992 | Fleenor |
| 5,234,429 A | 8/1993 | Goldhaber |
| 5,376,089 A | 12/1994 | Smith |
| 5,437,662 A * | 8/1995 | Nardella ........................ 606/38 |
| 5,484,434 A | 1/1996 | Cartmell et al. |
| 5,573,535 A | 11/1996 | Viklund |
| 5,626,577 A | 5/1997 | Harris |
| 5,800,431 A | 9/1998 | Brown |
| 5,807,392 A | 9/1998 | Eggers |
| 5,951,548 A | 9/1999 | DeSisto et al. |
| 5,951,551 A | 9/1999 | Erlich |

FOREIGN PATENT DOCUMENTS

WO  WO 92/05743  4/1992

* cited by examiner

Primary Examiner—Rosiland S. Kearney
(74) Attorney, Agent, or Firm—Caesar, Rivise, Bernstein, Cohen & Pokotilow, Ltd.

(57) ABSTRACT

An electrosurgical instrument having a working end that utilizes a coagulation surface and a cutting surface that can be moved relative to each other and wherein only one of the two surfaces is electrically enabled depending on their relative positions. The user can then depress a switch to activate the electrically enabled surface.

17 Claims, 5 Drawing Sheets

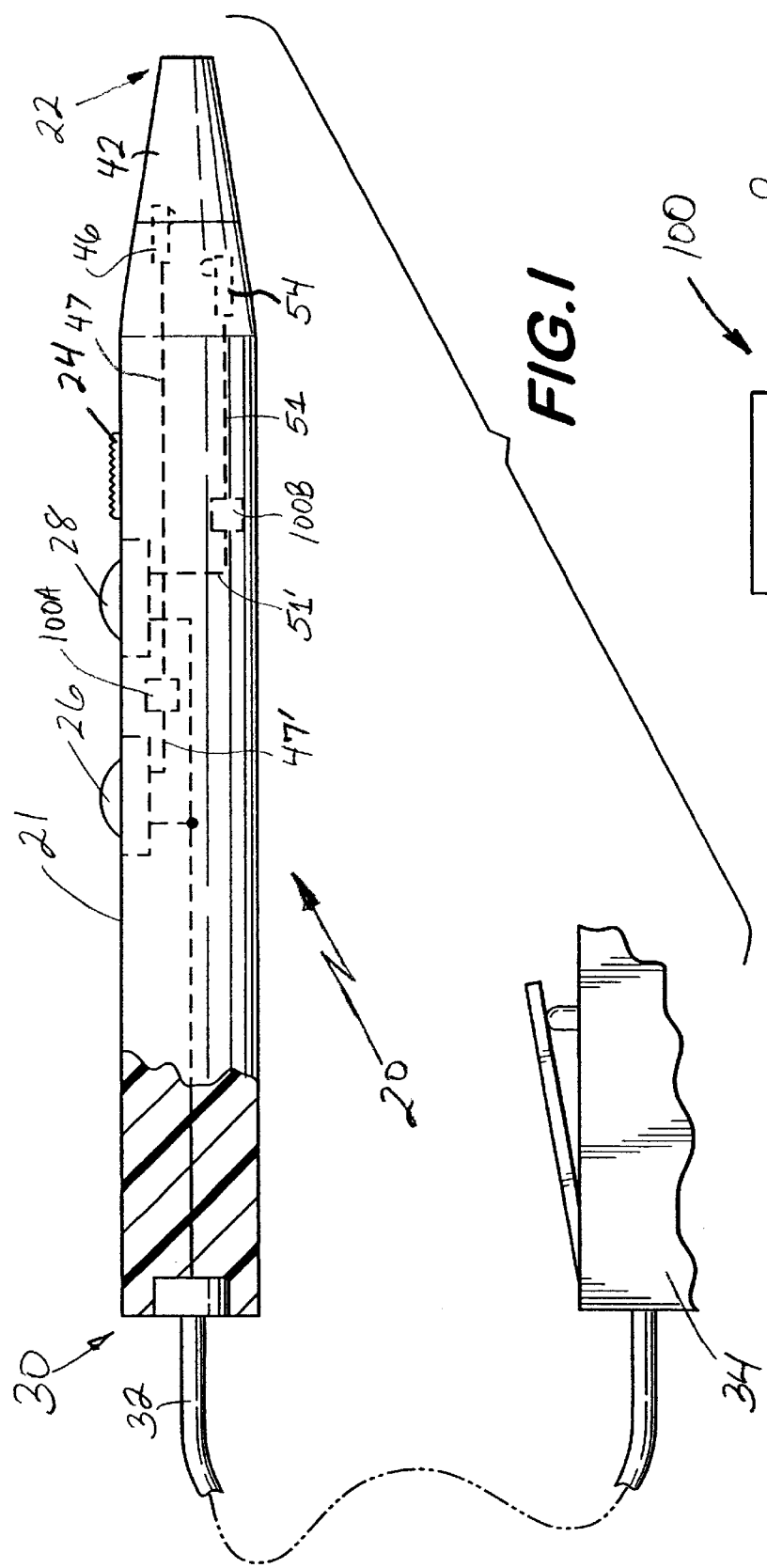
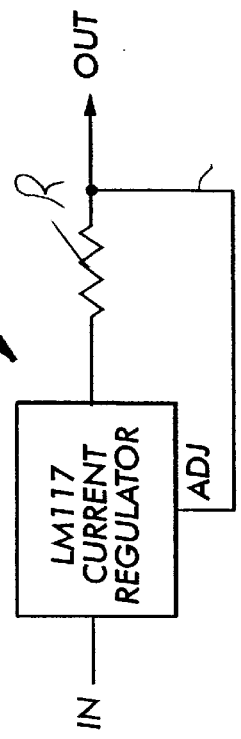
FIG.1
FIG.11

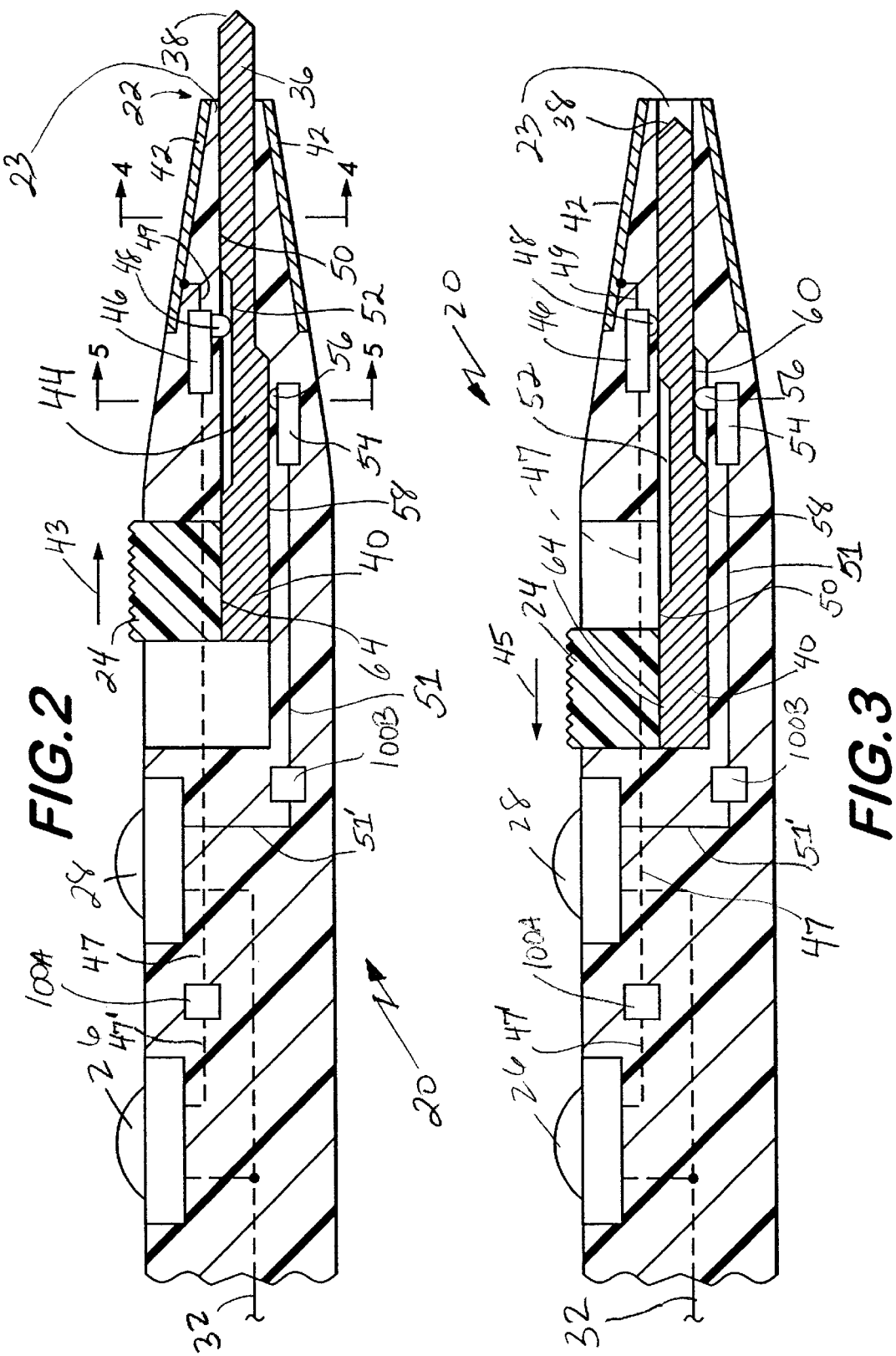

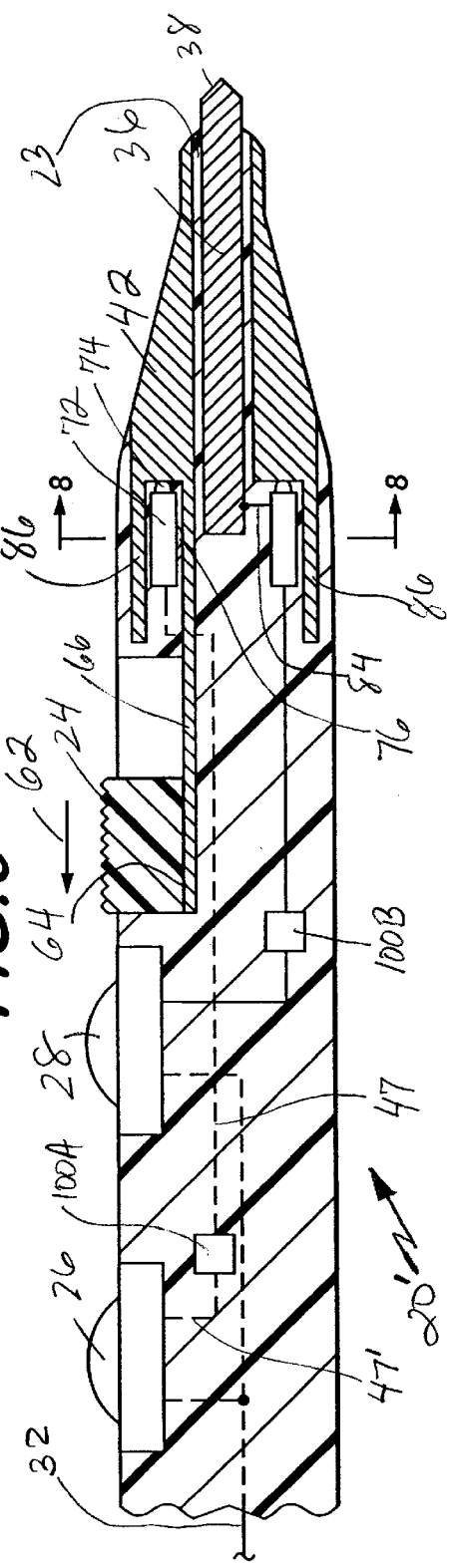
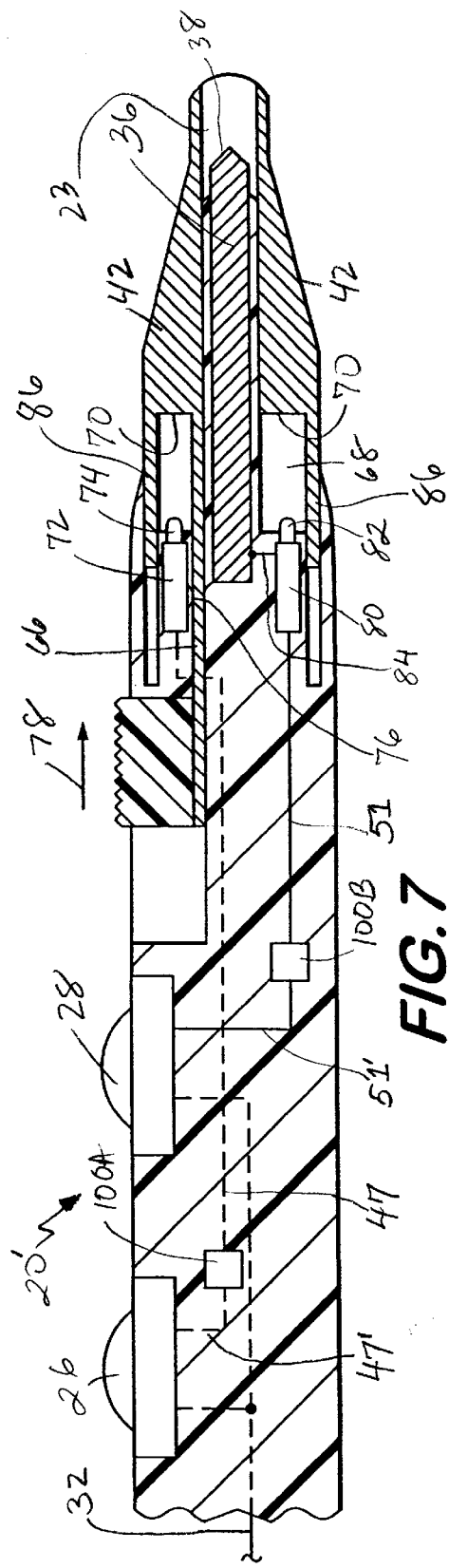

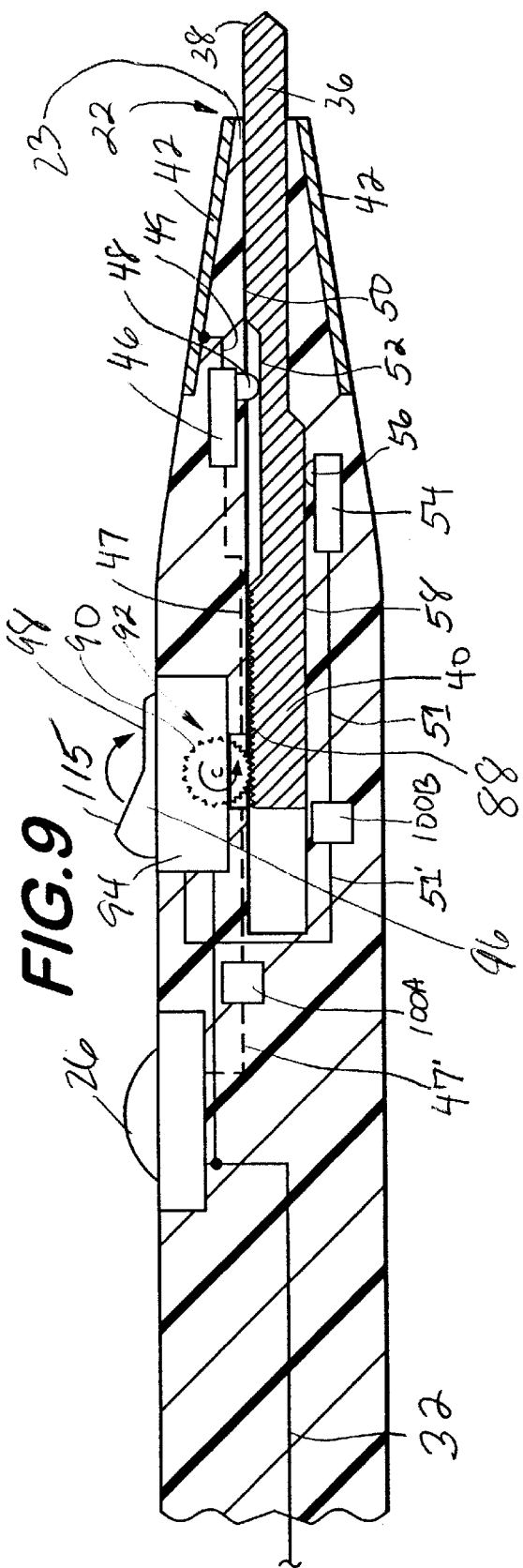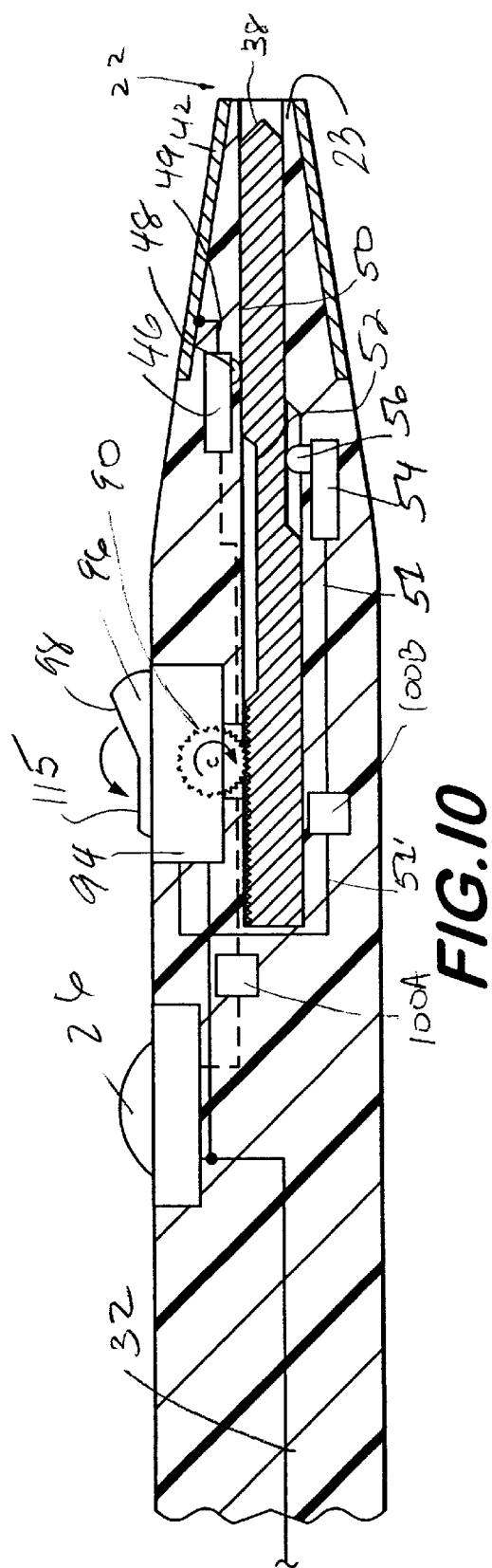

ELECTROSURGICAL INSTRUMENT WITH SEPARATE CUTTING AND COAGULATING MEMBERS

FIELD OF THE INVENTION

This invention relates generally to the field of medical devices and more particularly to electrosurgical cutting/coagulating instruments that can be specifically adapted for use in laparoscopic, endoscopic and open surgery surgical procedures.

BACKGROUND OF THE INVENTION

The principle of applying electrical current to living being tissue for the purposes of coagulating a bleeding organ or tissue, or for cutting tissue or an organ, is well-known in the art. By passing a certain level of electrical current through a tissue/organ, a coagulation of a bleeding area is accomplished. If the electrical current level is substantially increased, the passage of that higher level current acts to physically sever tissue. Many surgical devices incorporate these electrical cutting and/or coagulating features, such as insulated forceps, biopsy devices and clamping devices.

One well-known type of surgical device that permits a more focused application of electrical cutting and/or coagulating to living being tissue is generally referred to as an electrosurgical instrument, or more commonly referred to as a "Bovie". This type of instrument usually comprises an elongated single member having an electrically active tip. The instrument has the general appearance of a pen/pencil with a tapered tip that can be positioned directly onto the tissue being cauterized or cut. The electrosurgical instrument is electrically coupled to the power side of a power supply while the patient is positioned on a conductive plate electrically coupled to the ground of the power supply; the current path is formed from the power source, through the electrosurgical instrument, through the tissue being cut/coagulated and then into the conductive plate. Examples of these types of electrosurgical instruments are shown in U.S. Pat. Nos. 4,911,159 (Johnson et al.); U.S. Pat. No. 5,035,695 (Weber, Jr. et al.); U.S. Pat. No. 5,098,430 (Fleenor); U.S. Pat. No. 5,376,089 (Smith); U.S. Pat. No. 5,234,429 (Goldhaber); U.S. Pat. No. 5,484,434 (Cartmell et al.); U.S. Pat. No. 5,626,577 (Harris); U.S. Pat. No. 5,800,431 (Brown); U.S. Pat. No. 5,807,392 (Eggers); U.S. Pat. No. 5,951,548 (DeSisto et al.); U.S. Pat. No. 5,951,551 (Erlich). In some cases, a pair of opposing jaws can be used at the working end instead of a single member, such as that disclosed in U.S. Pat. No. 4,051,855 (Schneiderman).

In other cases, a bipolar configuration of the electrosurgical instrument is used whereby the flow of current is confined between a pair of electrodes at the working end of the electrosurgical instrument, rather than through the patient's body into a conductive plate. An example of such a bipolar configuration is shown in U.S. Pat. No. 5,573,535 (Viklund).

However, many of these electrosurgical instruments suffer from, among other things, the inadvertent application of a cutting current when only a coagulation current is desired, or vice versa. Furthermore, there is no way of providing the surgeon operating the instrument to have some sort of automatic feedback about what level of current is about to be applied. In addition, the positioning of the electrically-active tip of the electrosurgical instrument against the tissue does not always provide a precise application of the current to the tissue. Thus, there remains a need for an electrosurgical instrument that minimizes the chance of the inadvertent application of cutting or coagulating current to tissue, as well as minimizing the application of electrical and thermal contact of the electrically-active tip to surrounding tissue while providing the surgeon with automatic feedback about what level of current is about to be applied.

SUMMARY OF THE INVENTION

An apparatus for cutting and coagulating tissue during surgery of a living being while minimizing electrical and thermal contact of the apparatus with surrounding tissue. The apparatus is coupled to a power supply and wherein the living being is positioned on a conductive plate that is also coupled to the power supply. The apparatus comprises: an elongated body portion having a working end for alternately delivering a coagulation current to tissue through a first portion of the working end and for delivering a cutting current to tissue through a second portion of the working end and wherein the elongated body portion is electrically insulated except for the first portion and the second portion; the first portion comprises a tapered surface that forms the extreme end of the working end of the apparatus and wherein the first portion is electrically conductive and has an aperture therein; the second portion comprises an electrically conductive element having a tapered tip; the first portion and the second portion are movably coupled to each other so that the tapered tip can be positioned externally of the first portion or positioned within the first portion through the aperture; the second portion is electrically enabled whenever the second portion is positioned externally of the first portion while the first portion remains electrically disabled, defining a first apparatus state; wherein the first portion is electrically enabled whenever the second portion is positioned within the first portion and the second portion remains electrically disabled, defining a second apparatus state; and a switch for electrically energizing only the first portion in the first apparatus state when the switch is depressed and for electrically energizing only the second portion in the second apparatus state when the switch is depressed.

A method for cutting and coagulating tissue during surgery of a living being that is positioned on a conductive plate which is connected to a power supply while minimizing electrical and thermal contact of surrounding tissue. The method comprises the steps of: providing an electrosurgical instrument that is completely insulated except for a first and second portion of the working end of the instrument; coupling the instrument to the power supply and electrically enabling one of the portions while electrically disabling the other one of the portions depending on the relative positions of the first and second portions; electrically energizing the electrically enabled portion by a activating a switch to deliver a coagulating current or a cutting current to the tissue.

DESCRIPTION OF THE DRAWINGS

Many of the attendant advantages of this invention will be readily appreciated as the same becomes better understood by reference to the following detailed description when considered in connection with the accompanying drawings wherein:

FIG. 1 is a side elevation view, in partial cross-section, of the electrosurgical instrument having separate cutting and coagulating members coupled to a power source;

FIG. 2 is an enlarged cross-sectional view of the working end of a first embodiment of the present invention shown with the cutting member extended forward;

FIG. 3 is an enlarged cross-sectional view of the working end of the first embodiment of the present invention shown with the cutting member retracted;

FIG. 6 is an enlarged cross-sectional view of the working end of a second embodiment of the present invention shown with the coagulation member in a retracted position;

FIG. 7 is an enlarged cross-sectional view of the working end of a second embodiment of the present invention shown with the coagulation member extended forward;

FIG. 9 is an enlarged cross-sectional view of the first embodiment of FIG. 2 that uses an automatic extension/retraction mechanism to extend the cutting member;

FIG. 10 shows the embodiment of FIG. 9 with the cutting member in the retracted position; and FIG. 11 is a schematic of a current control circuit for providing the coagulation current level or the cutting current level.

DESCRIPTION OF THE PREFERRED EMBODIMENTS OF THE INVENTION

Figure 4:
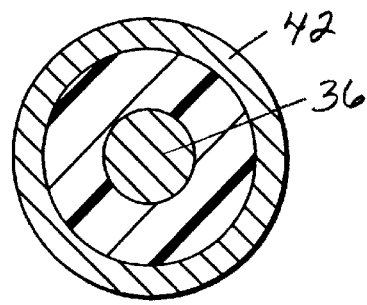
FIG. 4 is a cross-sectional view of the first embodiment taken along line 4—4 of FIG. 2.
Figure 5:
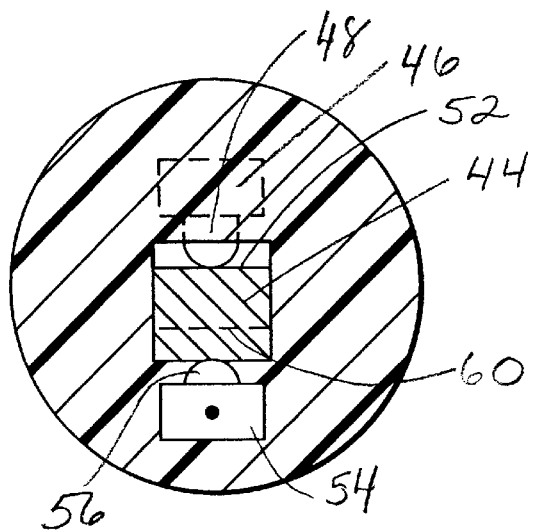
FIG. 5 is a cross-sectional view of the first embodiment taken along line 5—5 of FIG. 2.

Referring now in greater detail to the various figures of the drawing wherein like reference characters refer to like parts, an electrosurgical instrument with separate cutting and coagulating members (hereinafter "device") is shown at 20 in FIG. 1. In general, the device 20 comprises an elongated body portion 21 having a working proximal end 22 having a slider 24 that permits the surgeon to manually extend or retract a cutting tip from a surrounding coagulating surface, as will be described in detail later. Furthermore, there is a coagulating switch 26 and a cutting switch 28 that allows the surgeon to electrically activate either the coagulation surface or the cutting tip, respectively. As also will be described in detail later, the device 20 is completely insulated except for the coagulation surface and the cutting tip, both of which pass electrical current when activated. At the distal end 30 of the device 20, an electrical conductor 32 is secured for providing electrical energy to the coagulating surface or cutting tip when activated. The other end of the electrical conductor 32 may be coupled directly to a power source (not shown), or may be coupled to a foot pedal 34 (as will be discussed later) which in turn is coupled to the power source (not shown). The patient (not shown) lies on a conducting plate (also not shown) which is connected to the return of the power source. Thus, an electrical circuit is formed from the power source, through the electrical conductor 32, through the device 20, through the working proximal end 22, through the patient and then into the conducting plate and then back to the power source.

As shown most clearly in FIG. 2, the first embodiment of the device 20, the proximal end 22 comprises a central member 36 whose forward end comprises the cutting tip 38. The central member 36 is a conductor of electrical current. The back portion 40 of the central member 36 is coupled to the bottom surface 64 of the slider 24 such that when the surgeon moves the slider 24 forward in the direction of the arrow 43, the cutting tip 38 is extended outside of a coagulating surface 42, through an aperture 23. Alternatively, when the surgeon moves the slider 24 in the direction of the arrow 45 as shown in FIG. 3, the cutting tip 38 is retracted completely within the coagulating surface 42 through the aperture 23.

The middle portion 44 of the central member 36 is contoured to provide alternate electrical enablement of either the cutting tip 38 or the coagulation surface 42. In other words, only one of the two items, i.e., the cutting tip 38 or the coagulation surface 42, can be electrically enabled depending on the position of the central member 36. For example, as shown most clearly in FIG. 2, the central member 36 has been extended. A first internal electrical switch 46 has a contact 48 that rides along the upper surface 50 of the central member 36. This electrical switch 46 is electrically coupled to the coagulation switch 26, via an electrical conductor 47, a coagulation current control circuit 100A and another conductor 47' on one side and is electrically coupled to the coagulation surface 42 via another electrical conductor 49 on the other side of the switch 26. The coagulation current control circuit 100A provides the proper coagulation current level that passes to the coagulation surface 42, as will be discussed in detail later. Because the upper surface 50 of the central member 36 includes a depression 52 in the middle portion 44, the contact 48 moves downward which opens the electrical switch 46. As a result, no electrical current can pass through the electrical switch 46 and, therefore, even if the surgeon were to depress the coagulation switch 26, the coagulation surface 42 would remain inactive. Simultaneously, a second internal switch 54 has a contact 56 that rides along the bottom surface 58 of the central member 36. This electrical switch 54 is electrically coupled to the cutting switch 28 via an electrical conductor 51, a current control circuit 100B and another conductor 51'. The cutting current control circuit 100B provides the proper cutting current level that passes to the cutting tip 38, as will be discussed in detail later. As can be seen most clearly in FIG. 2, there is no depression in the bottom surface 58 of the middle portion 44 that directly corresponds to the depression 52 in the upper surface 50. As a result, the contact 56 is compressed and the second electrical switch 54 is closed, thereby forming an electrical current path from the electrical conductor 32, through the cutting switch 28, through the electrical switch 54, through the contact 56, through the central member 36 and then out through the cutting tip 38. Should the surgeon depress the cutting switch 28, electrical cutting current is then passed through the cutting tip 38. On the other hand, should the surgeon depress the coagulation switch 26 with the cutting member 36 extended, the coagulation surface 42 will remain unenergized because there is no current path formed. Thus, as shown in FIG. 2, the only item that can be electrically energized is the cutting tip 38 when the cutting switch 28 is depressed by the surgeon.

Alternatively, as shown most clearly in FIG. 3, if the surgeon retracts the central member 36 by moving the slider 24 in the direction of the arrow 45, a depression 60 in the bottom surface 58 of the central member 36 is now positioned over the contact 56, thereby allowing the contact 58 to move upward which opens the electrical switch 48. As a result, no electrical current can pass through the electrical switch 54 and, therefore, even if the surgeon were to depress the cutting switch 28 with the central member 36 in the retracted position, the cutting tip 38 would remain inactive. Simultaneously, because of the position of the central member 36, the depression 52 in the upper surface 50 of the central member 36 has been shifted backward causing the upper surface 50 to compress the contact 48 of the first switch 46 which closes the first switch 46. As a result, a current path is formed from the electrical conductor 32, through the coagulating switch 26, through the conductor 47, through the electrical switch 46, through the conductor 49 and then into the coagulating surface 42. Should the surgeon depress the coagulating switch 26, electrical coagulating current is then passed through the coagulation surface 42.

It should be understood that it is within the broadest scope of this invention to include the foot pedal 34 that can replace both the coagulating switch 26 and the cutting switch 28. In particular, when the single foot pedal 34 is used, the switches 26/28 would not be present and the conductors 47' and 51' would be connected together and coupled to the electrical conductor 32. When the surgeon is ready to activate the particular item, namely the cutting tip 38 or the coagulating surface 42, he/she would step on the foot pedal 34 and, in accordance with the above discussion, only one of the two items would be electrically active, depending on the position of the center member 36.

A second embodiment 20' of the device is depicted in FIGS. 6 and 7 whereby the central member 36 remains fixed and the outer coagulating surface 42 can be moved outward to cover the cutting tip 38 or moved inward to expose the cutting tip 38. In particular, in FIG. 6, the coagulating surface 42 is shown displaced backward (i.e., the slider 24 has been moved in the direction of the arrow 62) such that the cutting tip 38 is exposed. In this embodiment, the central member 36 is fixed inside the device 20'. As can be seen in FIG. 6, the bottom surface 64 of the slider 24 has been coupled to a conducting driving member 66 that is coupled to the interior of the coagulating surface 42. Furthermore, the interior of the coagulating surface 42 is shaped to form a recess 68 when the coagulating surface 42 is extended forward (FIG. 7) and can be minimized such that an interior surface 70 can be used to drive the contacts of two electrical switches into the switch bodies. These switches are configured oppositely so that the compression of the contact of one switch closes the switch while the extension of the contact of the other switch opens the switch, as is discussed next.

The upper electrical switch 72 is electrically coupled to the coagulating switch 26 through the conductor 47, the coagulation current control circuit 100A and the conductor 47. A contact 74 is compressed whenever the interior surface 70 is slid against the contact 74. The switch 72 is electrically coupled to the driving member 66 through a pole 76. Thus, when the contact 74 is compressed, the switch 72 is configured to be opened, thereby preventing any current from passing to the coagulating surface 42. Alternatively, when the slider 24 is slid forward in the direction of the arrow 78 (FIG. 7), the contact 74 is extended, thereby closing the switch 72 and forming a current path from the electrical conductor 32, through the coagulating switch 26, through the conductor 47', through the coagulation current control circuit 100A, through the conductor 47, through the electrical switch 72, through the driving member 66 and then into the coagulating surface 42.

The lower electrical switch 80 is electrically coupled to the cutting switch 28 through the conductor 51, the cutting current control circuit 100B and the conductor 51'. A contact 82 is compressed whenever the interior surface 70 is slid against the contact 82. The switch 80 is electrically coupled to the central member 36 via a conductor 84. Thus, when the contact 82 is compressed, the switch 80 is configured to be closed, thereby forming a current path from the electrical conductor 32, through the cutting switch 28, through the conductor 51', through the cutting current control circuit 100B, through the conductor 51, through the electrical switch 80, through the conductor 84 and then into the central member 36. Alternatively, when the coagulating surface is moved in the direction of the arrow 78 (FIG. 7), the switch 80 is opened, thereby preventing any current from passing to the cutting tip 38.

In light of the above switch configurations, when the coagulating surface 42 is moved backward in the direction of the arrow 62 (FIG. 6), upon depressing the cutting switch 28, the cutting tip 38 is activated with the coagulating surface 42 remaining de-energized even if the coagulating switch 26 is depressed. Alternatively, when the coagulating surface 42 is moved forward in the direction of the arrow 78 (FIG. 7), upon depressing the coagulating switch 26, the coagulating surface 42 is activated with the cutting tip 38 remaining de-energized even if the cutting switch 28 is depressed.

Figure 8:
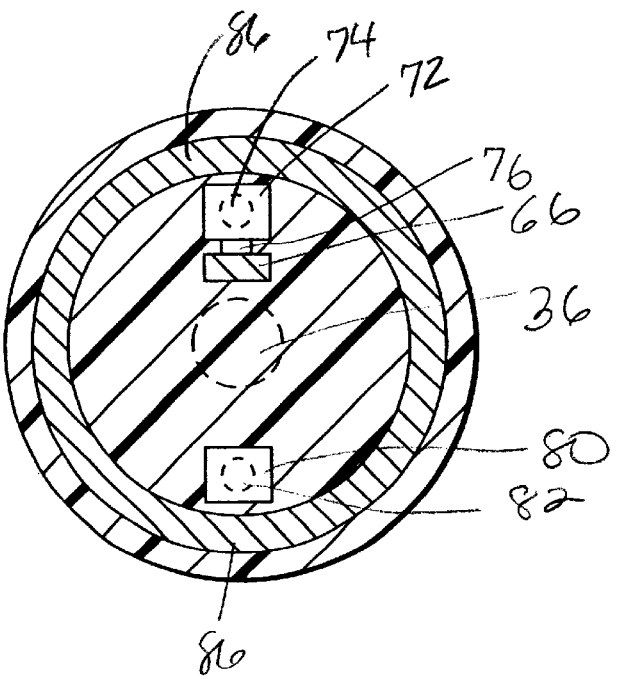
FIG. 8 is a cross-sectional view of the second embodiment taken along line 8—8 of FIG. 6.

It should be noted that because the coagulating surface 42 can be moved forward and backward, a cover extension 86 (FIGS. 6–8) is necessary to cover the recess 68 when the coagulating surface 42 is moved forward to prevent the ingress of body fluids, etc.

FIGS. 9 and 10 depict another variation of the first embodiment that utilizes an automatic extension/retraction mechanism, rather than the manual slider 24 discussed previously. The electrical switches 46/54 operate the same as discussed previously with regard to the first embodiment. In the variation shown in FIGS. 9 and 10, the back portion 40 of the upper surface 50 of the central member 36 comprises teeth or serrations 88 that interdigitate with the teeth/serrations 90 of a wheel 92. The wheel 92 is driven by a miniature actuator 94 that is activated with a switch 96. When the forward surface 98 of the switch 96 is depressed as shown in FIG. 9, the actuator 94 rotates the wheel 92 to precisely drive the cutting tip 38 forward into the exposed position shown in FIG. 9, while electrically energizing the tip 38. Alternatively, when the back surface 115 of the switch 96 is depressed as shown in FIG. 10, the actuator 94 rotates the wheel 92 in the opposite direction to precisely drive the cutting tip 38 backward into the fully retracted position shown in FIG. 10. The surgeon can then depress the coagulation switch 26 to energize the coagulating surface 42.

It should be understood that it is within the broadest scope of the present invention to have the actuator 94/switch 96 replace the coagulation switch 26 of the second embodiment 20' in order to automatically extend or retract the coagulation surface 42 while electrically energizing that surface 42 when extended forward (direction of arrow 78, FIG. 7) and electrically disabling that surface 42 when retracted back (direction of arrow 62, FIG. 6).

FIG. 11 is a schematic of the coagulation current control circuit 100A and the cutting current control circuit 100B. These circuits 100 can be implemented using a Motorola LM117 current regulator configured as shown. In particular, in the first and second embodiments, the conductors 47' or 51' are connected to the input of the LM117 and the conductors 47 or 51 are connected to the output of the LM117. The resistor R is determined to provide the proper current level, depending on how the LM117 is used: either for coagulation or for cutting.

It should be understood that the based on the position of the slider 24, or the switch 96, the surgeon is automatically provided with feedback about what current level is about to be applied to the tissue. For example, in the embodiment of FIGS. 1–5, when the surgeon slides the slider 24 in the direction 43, he/she knows that cutting current is enabled; conversely, by sliding the slider 24 in the direction 45, the surgeon knows that coagulating current is enabled.

Without further elaboration, the foregoing will so fully illustrate my invention that others may, by applying current or future knowledge, readily adopt the same for use under various conditions of service.

What is claimed is:

1. An apparatus for cutting and coagulating tissue during surgery of a living being while minimizing electrical and thermal contact of said apparatus with surrounding tissue, said apparatus being coupled to a power supply and wherein the living being is positioned on a conductive plate that is also coupled to the power supply, said apparatus comprising:

an elongated body portion having a working end for alternately delivering a coagulation current to tissue through a first portion of said working end and for delivering a cutting current to tissue through a second portion of said working end, said elongated body portion being electrically insulated except for said first portion and said second portion;

said first portion comprising a tapered surface that forms the extreme end of the working end of said apparatus, said first portion being electrically conductive and having an aperture therein;

said second portion comprising an electrically conductive element having a tapered tip;

said first portion and said second portion being movably coupled to each other so that said tapered tip can be positioned externally of said first portion or positioned within said first portion through said aperture;

wherein movement of said second portion externally of said first portion causes said second portion to be electrically enabled while causing said first portion to be electrically disabled, defining a first apparatus state;

wherein movement of said second portion internally of said first portion causes said first portion to be electrically enabled while causing said second portion to be electrically disabled, defining a second apparatus state; and a switch for electrically energizing only said first portion in said first apparatus state when said switch is depressed and for electrically energizing only said second portion in said second apparatus state when said switch is depressed.

2. The apparatus of claim 1 wherein said switch comprises a foot pedal switch.

3. The apparatus of claim 1 wherein said switch comprises a first and second switch on said elongated body portion, said first switch electrically energizing only said first portion in said first apparatus state when said first switch is activated and wherein said second switch electrically energizes only said second portion in said second apparatus state when said second switch is activated.

4. The apparatus of claim 1 wherein said second portion can be moved in a first direction to extend out of said first portion through said aperture and can be moved in a second opposite direction to be retracted into said first portion through said aperture.

5. The apparatus of claim 1 wherein said first portion can be moved in a first direction to cover said second portion and can be moved in a second opposite direction to expose said second portion.

6. The apparatus of claim 4 further comprising a manually-operated slider that permits the user to move said second portion in said first and second directions.

7. The apparatus of claim 5 further comprising a manually-operated slider that permits the user to move said first portion in said first and second directions.

8. The apparatus of claim 1 wherein said switch comprises a first and second switch on said elongated body portion, said first switch having a first and second activation position, said first activating position driving said second portion out of said first portion through said aperture while electrically energizing said second portion and while electrically disabling said first portion.

9. The apparatus of claim 8 wherein said second activating position drives said second portion into said first portion through said aperture while electrically disabling said second portion while electrically enabling said first portion, said first portion being electrically energized when said second switch is activated.

10. The apparatus of claim 1 wherein said switch comprises a first and second switch on said elongated body portion, said first switch having a first and second activation position, said first activating position driving said first portion in a first direction to cover said second portion while electrically activating said first portion and while electrically disabling said second portion.

11. The apparatus of claim 10 wherein said second activating position drives said first portion in a second opposite direction to expose said second portion through said aperture while electrically disabling said first portion, said second portion being electrically energized when said second switch is activated.

12. The apparatus of claim 1 further comprising a coagulation current control circuit that modifies the current supplied by the power supply to deliver a coagulating current level through said first portion.

13. The apparatus of claim 1 further comprising a cutting current control circuit that modifies the current supplied by the power supply to deliver a cutting current level through said second portion.

14. A method for cutting and coagulating tissue during surgery of a living being that is positioned on a conductive plate which is connected to a power supply while minimizing electrical and thermal contact of surrounding tissue, said method comprising the steps of:

(a) providing an electrosurgical instrument that is completely insulated except for a first and second portion of the working end of said instrument;

(b) coupling said instrument to the power supply and electrically enabling one of said portions while electrically disabling the other one of said portions depending on the relative positions of said first and second portions, wherein said step of electrically enabling one of said portions comprises extending said second portion outwardly from said first portion and whereby extending said second portion causes said first portion to be electrically disabled and causes said second portion to be electrically enabled, or wherein said step of electrically enabling one of said portions comprises retracting said second portion inwardly of said first portion and whereby retracting said second portion causes said second portion to be electrically disabled and causes said first portion to be electrically enabled; and (c) electrically energizing said electrically enabled portion by a activating a switch to deliver a coagulating current or a cutting current to the tissue.

15. The method of claim 14 wherein said step of electrically energizing said electrically enabled portion comprises:

(a) receiving power supply current from the power supply; and (b) diverting said power supply current to a coagulating current control circuit for delivering said coagulating current and to a cutting current control circuit for delivering said cutting current.

16. A method for cutting and coagulating tissue during surgery of a living being that is positioned on a conductive plate which is connected to a power supply while minimizing electrical and thermal contact of surrounding tissue, said method comprising the steps of:

(a) providing an electrosurgical Instrument that is completely insulated except for a first and second portion of the working end of said instrument;

(b) coupling said instrument to the power supply and electrically enabling one of said portions while electrically disabling the other one of said portions depending on the relative positions of said first and second portions, wherein said step of electrically enabling one of said portions comprises extending said first portion outwardly to cover said second portion and whereby said second portion is electrically disabled and said first portion is electrically enabled, or wherein said step of electrically enabling of one of said portions comprises retracting said first portion to expose said second portion and whereby said first portion is electrically disabled and said second portion is electrically enabled; and (c) electrically energizing said electrically enabled portion by a activating a switch to deliver a coagulating current or a cutting current to the tissue.

17. The method of claim 16 wherein said step of electrically energizing said electrically enabled portion comprises:

(a) receiving power supply current from the power supply; and (b) diverting said power supply current to a coagulating current control circuit for delivering said coagulating current and to a cutting current control circuit for delivering said cutting current.

* * * * *